(12) United States Patent
Floessholzer et al.

(10) Patent No.: US 9,820,815 B2
(45) Date of Patent: Nov. 21, 2017

(54) SKIN TREATMENT DEVICE WITH MEANS FOR PROVIDING A TACTILE FEEDBACK SIGNAL

(75) Inventors: Hannes Uwe Floessholzer, Klagenfurt (AT); Joldert Maria Rene Boersma, Eindhoven (NL); Gertrude Riëtte Van Der Kamp, Groningen (NL); Arif Veendijk, Assen (NL); Peter Eshuis, Deventen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1252 days.

(21) Appl. No.: 12/678,753

(22) PCT Filed: Sep. 16, 2008

(86) PCT No.: PCT/IB2008/053756
§ 371 (c)(1),
(2), (4) Date: May 27, 2010

(87) PCT Pub. No.: WO2009/037641
PCT Pub. Date: Mar. 26, 2009

(65) Prior Publication Data
US 2010/0241109 A1    Sep. 23, 2010

(30) Foreign Application Priority Data
Sep. 21, 2007  (EP) .................................... 07116944

(51) Int. Cl.
*A61B 18/20*  (2006.01)
*A61B 17/00*  (2006.01)
*A61B 18/00*  (2006.01)
*A61B 90/00*  (2016.01)

(52) U.S. Cl.
CPC ... *A61B 18/203* (2013.01); *A61B 2017/00115* (2013.01); *A61B 2018/00452* (2013.01); *A61B 2018/00476* (2013.01); *A61B 2090/395* (2016.02)

(58) Field of Classification Search
CPC ..................................................... A61B 18/20
See application file for complete search history.

(56) References Cited

U.S. PATENT DOCUMENTS

| | | | |
|---|---|---|---|
| 6,171,302 B1 | 1/2001 | Talpalriu et al. | |
| 6,659,007 B1 * | 12/2003 | Winston | 101/329 |
| 6,660,000 B2 | 12/2003 | Neuberger et al. | |
| 6,758,845 B1 | 7/2004 | Weckwerth et al. | |
| 7,220,254 B2 | 5/2007 | Altshuler | |
| 2002/0120256 A1 | 8/2002 | Furuno et al. | |
| 2004/0147984 A1 | 7/2004 | Altshuler et al. | |
| 2006/0020260 A1 * | 1/2006 | Dover et al. | 606/9 |
| 2007/0005047 A1 | 1/2007 | Ferren et al. | |

FOREIGN PATENT DOCUMENTS

WO    2006092776 A1    9/2006

* cited by examiner

*Primary Examiner* — Lynsey Eiseman

(57) ABSTRACT

A skin treatment device having a treatment window for treating skin through the treatment window and a user guide to deliver a tactile feedback signal during movement in stepwise increments of the treatment window along the skin.

13 Claims, 10 Drawing Sheets

Moving direction

SKIN TREATMENT DEVICE WITH MEANS FOR PROVIDING A TACTILE FEEDBACK SIGNAL

FIELD OF THE INVENTION

The present invention relates to a skin treatment device having a treatment window for treating skin through the treatment window and user guidance means for aiding a user of the skin treatment device in moving the treatment window along the skin in a stepwise manner, each moving step having a finite step width by which the treatment window is displaced. More particularly, it relates to a photoepilator.

BACKGROUND OF THE INVENTION

Photoepilation is a well-established technique for removing hair on the human skin and for temporarily preventing the growth of new hair. Before the actual epilation, the skin to be epilated is shaven. In the subsequent photoepilation step, the part of the skin that is to be epilated is exposed to intense light, typically in the form of a flash from a laser source, wherein the light is emitted through a treatment window. The treatment window is usually rectangular and has a cross section of a few square centimeters. In order to treat a larger area of the skin, the treatment window (and with it the entire treatment device) is moved over the skin in a stepwise manner, each step including the emission of a light flash, so that a different area of the skin is treated in each step. The wavelength of the laser light is chosen so as to be significantly absorbed by the hair sacks (follicles) in the skin. The absorbed radiation transforms into heat, thereby "inactivating" the follicles so that they will not produce new hair during a certain period after the treatment, typically about four weeks. After that period, the treatment has to be repeated for the skin to remain hair-free.

Although state-of-the art optical epilators use lasers as the light source, the light for photoepilation needs to be neither monochromatic nor coherent. The reasons for using lasers to generate the radiation are rather practical ones, such as a laser's small size, its limited frequency spectrum, high energy efficiency, high intensity and low cost. It is stressed that the present invention includes optical skin treatment devices in which the electromagnetic radiation used for treatment is generated by means other than a laser, for example by means of a broadband intense pulsed light source or flash lamp. It is further stressed that the present invention does not only include optical skin treatment devices for hair removal or hair growth reduction in general, but also includes optical skin treatment devices for other dermatological purposes such as, for example, skin rejuvenation, acne treatment, the treatment of psoriasis, etc.

The invention also applies to non-optical forms of surface treatment in which a surface, which is not necessarily skin, is to be treated in a stepwise manner via a treatment window. Examples of non-optical forms of surface treatment include applying RF energy, ultrasound energy, a liquid or paste, such as a lotion, oil or paint, to the surface via a treatment window, or plasma treatment via a treatment window, e.g. for sterilization or cleaning.

A problem of photoepilation and other optical skin treatment methods and devices is that the light incident on the skin does not immediately leave any visible mark on the skin. In fact, the effects of the exposure to light only manifest themselves in the reduced rate of hair growth or other dermatological result in the days or weeks following the treatment. Hence a lot of attention is needed during the treatment in order to expose every part of the skin that is to be epilated or otherwise treated, while avoiding exposing any part more than once. Indeed, a repeated treatment of the same area can be potentially harmful due to the additional amount of energy absorbed. In order to help the user in displacing the treatment window over the skin, state-of-the art optical skin treatment devices are provided with feedback means informing the user about the motion of the device and/or about the surface that has already been treated. The majority of these feedback means are designed to deliver optical or acoustic signals, for example, an LED that is illuminated when the skin treatment device has been moved by a distance corresponding to the width of the treatment window. Also in other forms of surface treatment (e.g. plasma surface treatment), the present invention will be especially useful when the effect of the treatment is not immediately visible to the naked eye.

U.S. Pat. No. 6,171,302 B1 discloses an apparatus and a method for synchronizing the activation of a light source with the position of a handpiece on a surface and for providing a substantially uniform exposure of a surface to light radiation. The handpiece, which is moved along the surface by an operator, includes a sensor for sensing the distance traversed by the handpiece on the surface. The sensor sends signals to a signal processing unit which calculates the distance traversed by the handpiece on the surface.

Providing the operator of a surface treatment device merely with optical or acoustic feedback signals has the disadvantage that the operator needs to interpret these signals correctly. Therefore, operating the device usually requires some training. In fact, photoepilation is nearly always performed by a professional therapist. Providing only optical feedback signals further has the disadvantage that the user would find it difficult to receive the optical signals when he or she were to apply the skin treatment device on parts of his (her) own body that he (she) cannot directly see, such as parts of his (her) back. Furthermore, state-of-the art feedback systems involve fairly complex electronics for evaluating the distance by which the treatment device has been moved along the surface to be treated and for triggering the feedback signal. The state-of-the-art feedback systems are rigidly integrated in the treatment device. However, it would be desirable to have user feedback means which can be flexibly adjusted to different operating parameters or to personal preferences of the user or the patient.

It is therefore an object of the present invention to provide a skin treatment device having a treatment window for treating skin through the treatment window and user guidance means for aiding a user of the skin treatment device in moving the treatment window along the skin in a stepwise manner, each moving step having a finite step width by which the treatment window is displaced, wherein the user guidance means are to be simple, easily modifiable, and to provide the user with easy-to-interpret feedback signals.

This object is achieved by the features of the independent claim. Further specifications and preferred embodiments of the invention are outlined in the dependent claims.

SUMMARY OF THE INVENTION

The invention provides a skin treatment device having a treatment window for treating skin through the treatment window and user guidance means for aiding a user of the skin treatment device in moving the treatment window along the skin in a stepwise manner, each moving step having a finite step width by which the treatment window is displaced, characterized in that the user guidance means are arranged separate from the treatment window and in that they deliver a tactile feedback signal to the user at each moving step. The user may be either the patient himself, i.e. the person whose skin is treated, or a different person. Accordingly, the feedback signal may be delivered either to the skin of the patient or to the hand of the user who operates the skin treatment device, or to both. The tactile feedback signal enables the user to feel the transition between two consecutive moving steps and/or enables informing him when the treatment window has reached a new correct position for treatment. The tactile feedback signal may be generated in different ways, as will become clear from the discussion of various embodiments. Arranging the user guidance means separate from the treatment window allows for more flexibility in designing specific embodiments of the user guidance means, for example, when the step width of the skin treatment device is to be dimensioned so as to differ from the dimension of the treatment window. User guidance means that are situated separate from the treatment window can be easier to access mechanically, which may be desirable, for instance, when a specific version of user guidance means is to be replaced by an alternative version. Furthermore, the user guidance means can be arranged such that they come into contact chiefly with those parts of the skin that have not yet been treated, which will be advantageous if the skin is irritated by the treatment. Providing a tactile feedback signal about the stepwise motion of the treatment window has the advantage that it can be delivered directly to those body parts implicated in the treatment, that is, either the skin of the patient or the hand of the user. Since a large part of the user's attention will be focused on his hand and/or on the skin that is treated (if the user is also the patient), the user is likely to be more attentive to a tactile signal as compared to an optical or acoustic signal, and will thus find the skin treatment device easier to use.

In a preferred embodiment of the invention, the step width measures between 90% and 100%, preferably about 95%, of the projection of the treatment window onto the moving direction. By choosing the step width to be somewhat smaller than the projection of the treatment window, a small overlap between consecutively exposed skin portions is achieved, which may ensure a more uniform exposure of the total area of the skin that is treated in the case where the intensity of the light is substantially lower near the edge of the treatment window. In this context, it is preferable that the treatment window be essentially rectangular and aligned parallel to the moving direction. However, the treatment window may have any other shape. In particular, it could be oval, circular, or triangular. In the case of a treatment window having the shape of a regular triangle, the skin treatment device could be moved in a stepwise manner by rotating it in each moving step by 60° about one of the three axes extending from the three corners of the triangle perpendicularly to the treatment window.

According to a preferred embodiment of the invention, the user guidance means include at least one step roller. The step roller is understood to include a rotative element that can be rolled on the patient's skin in a stepwise manner, such that each rotative step of the step roller translates into a displacement of the treatment window along the skin, thereby defining the step width. A step roller can be realized, for example, by a wheel having a polygonal contour, wherein each side of the polygon has a length equal to the step width. Advantageously, the rotative element is rotatable about a rotational axis parallel to the skin and perpendicular to the moving direction. The contour of the rotative member which comes into contact with the skin during the stepwise motion of the treatment window does not need to be cornered; it may in particular be circular, with a tactile signal being generated at particular rotational angles, for example, by providing a number of energetically preferred angles at which the rotational element assumes a minimum in internal potential energy. Such potential energy minima can be realized, for example, by providing an axle of the rotative element with notches, each notch corresponding to a specific rotational angle, together with a spring leaf that engages one of the notches when the rotational angle comes to coincide with one of the preferred angles and which disengages when the rotative element is rotated out of the preferred angle. A polygonal contour is likely to provide a firmer position of the rotative element on the skin between two consecutive moving steps, while a rotative element having a circular contour may be more comfortable to roll.

According to a specific embodiment of the invention, the at least one step roller is replaceable by a different step roller. This can be very convenient, for example, when the treatment window is essentially rectangular, thus defining two preferred moving directions (i.e. the rectangle's symmetry axis). In this case it is advantageous to optimize the two step rollers for the two preferred moving directions. More precisely, each step roller's rotational axis ought to be perpendicular to the respective moving direction, and its step width ought to be adapted to the rectangle's projection onto the respective moving direction. The at least one step roller and the different step roller may be both detachable from and re-attachable to the skin treatment device, so that exchanging them includes removing one and attaching the other. Alternatively, both step rollers may be permanently integrated in the skin treatment device. In a specific embodiment of the invention, both step rollers are integrated in a rotative element having essentially the form of a cuboid, wherein the cuboid is rotatable about two of its three principal axes.

According to another aspect of the invention, the user guidance means are elastically biased toward the skin, preferably by means of a spring. Thereby it is ensured that the user guidance means stay in firm mechanical contact with the skin, provided the user holds the skin treatment device sufficiently close to the skin. This then ensures that the tactile signal is correctly transmitted to the user. In embodiments where only the user guidance means are to contact the patient's skin while the rest of the skin treatment device does not contact the skin, the elastic force felt by the user (either via his or her hand, and, if the user is also the patient, via his or her skin) helps the user to easily assess or "feel" the distance between the treatment window and the skin.

It may further be advantageous that the user guidance means are at least partly detachable from the skin treatment device. For example, the user guidance means may be fixed to the skin treatment device by means of a movable bar to ensure that the user guidance means follow the patient's body curvatures. The movable bar could also allow to put the user guidance means into a stow-away position, for situations in which the user guidance means are not needed or found inconvenient (for example, when applying the skin treatment device to confined areas of the body such as armpits). The user guidance means might also be designed to be completely detachable in the sense that they can be completely taken off the skin treatment device and put aside, for example, for cleaning.

According to a preferred embodiment of the invention, the user guidance means are arranged to trigger an emission of light via the treatment window after each moving step. Such a mechanism allows for a very convenient way of treating large areas of the patient's skin by displacing the skin treatment device in the described stepwise manner along the skin. After each displacement, felt by the user through the tactile feedback signal, the skin treatment device automatically emits the necessary quantity of light via the treatment window, preferably in the form of a short flash. Thus, the user will not have to actuate any other means for triggering the emission. Repositioning the device, preferably felt by overcoming some kind of mechanical resistance generated by the user guidance means in cooperation with the skin, suffices to perform the next treatment step.

According to yet another embodiment of the invention, the user guidance means are arranged to trigger an optical or acoustic signal during or after each moving step. In the spirit of the invention, the optical or acoustic signal is complementary to the tactile feedback signal and may serve to inform the user that a moving step has been completed and that the skin treatment device is again ready to emit light via the treatment window. In the case where the emission via the treatment window is triggered automatically after each moving step as described above, the acoustic or optical signal is advantageously given during the emission, thereby informing the user that the light is indeed emitted.

According to another preferred embodiment of the invention, the skin treatment device includes marking means coupled to the user guidance means, for applying an optical mark to the skin during or after each moving step. In fact, in many common skin treatment procedures the effect of the treatment becomes apparent only after a period of many hours, possibly weeks. Therefore, when treating larger portions of the skin, which necessitates many moving steps and may involve interrupting the treatment, it is important to memorize the parts of the skin that have been treated. This is done most easily by marking them optically, for example, in the case of a rectangular treatment window, by indicating the four corners of the rectangular area on the skin that has been exposed to light. Since an optical mark may modify the absorption characteristics of the skin, the mark is preferably applied immediately after the respective area of skin has been treated, that is, after the emission of light through the treatment window but before repositioning the treatment window. For non-optical forms of skin treatment, such as the application of a lotion, paste or oil to the skin, it may however be advantageous to design the marking means such that a visible mark is applied before each treatment step, for example, if a lotion applied to the skin does not allow setting a visible mark. Hence a visible mark could be put on the skin such that it remains on the skin when the material (e.g. the paste) is applied onto the skin and when the material is removed/washed off the skin. In this context it is preferred that the marking means include at least one pencil for applying the optical mark.

According to the invention, the skin treatment device includes a blocking mechanism that, after each moving step, prevents the user from performing a new moving step at least until the treatment through the treatment window can resume. The blocking mechanism addresses the problem that a certain minimum time gap may be necessary between two successive treatment steps via the treatment window. In particular, a conventional pulsed laser used for photoepilation may need to "rest" for several seconds after emitting a light flash before it is capable of emitting the next flash. The blocking mechanism could be realized technically for example by means of an electronic or mechanical timer which is coupled to the triggering mechanism of the light source. The timer would then release the blocking mechanism only after a certain time lapse. Alternatively, the blocking mechanism could be released upon detection that the treatment can continue, for example, in the case where the treatment is performed using a pulsed laser, by detecting that the laser is ready to emit the next pulse. Then a timer would not be needed. When the user guidance means comprise a step roller, the blocking mechanism may be designed so as to prevent or render difficult a rotation of the step roller until the treatment can be continued.

These and other aspects of the invention will be further elucidated with reference to the embodiments described hereinafter.

DESCRIPTION OF PREFERRED EMBODIMENTS

Figure 1:
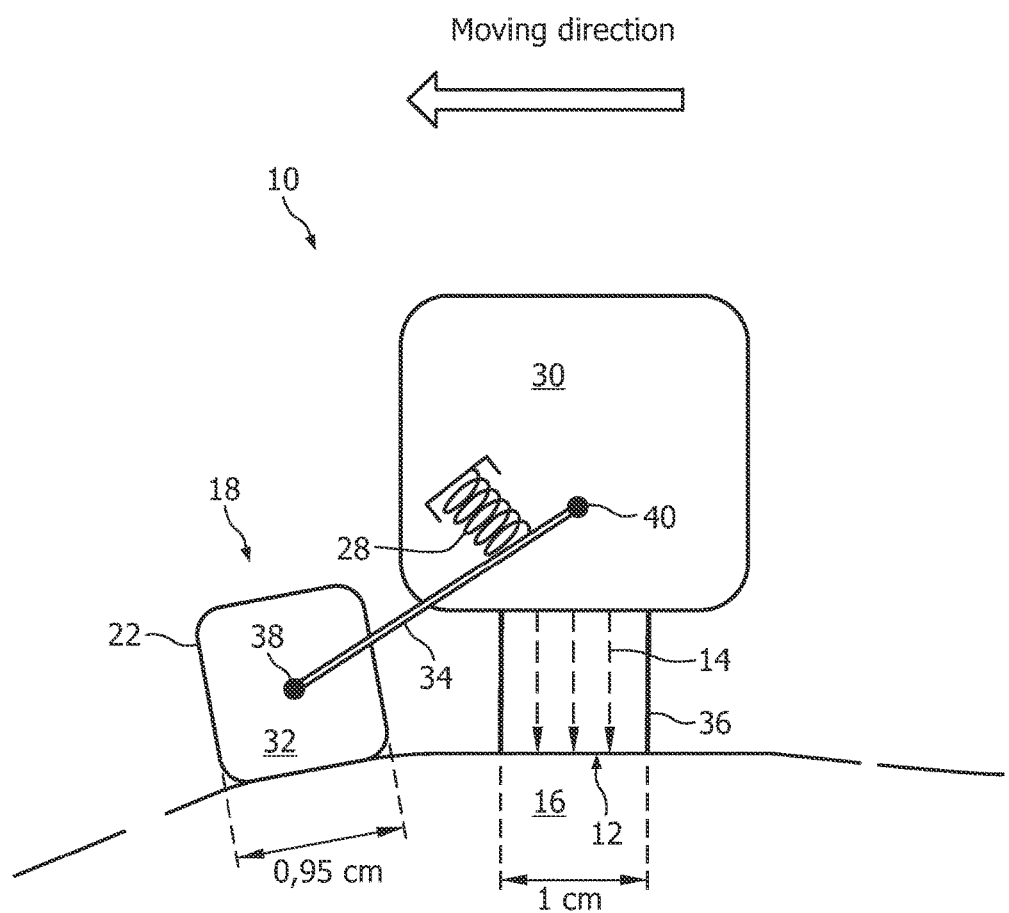
FIG. 1 is a schematic side view of a skin treatment device having a separate step roller.

In the drawings, similar or analogous features appearing in different Figures are designated using the same reference numerals and are not necessarily described more than once.

FIG. 1 is a side view of a first embodiment of the skin treatment device according to the invention. The skin treatment device 10 includes a handpiece 30 containing a laser (not shown) for generating a beam of light 14 emitted onto skin 16 through a hollow light guard 36 attached to the handpiece 30. The light 14 exits the hollow light guard via a treatment window 12 defined by the inner contour of the hollow light guard 36 at the guard's distal end contacting the skin during operation of the device 10. Attached to the handpiece 30 are user guidance means 18 comprising a wheel 32, a spring 28, and a lever 34 joining the wheel 32 to the handpiece 30. A distal part 38 of the lever 34 forms an axle for the wheel 32, so that the wheel 32 is rotatable about the axle 38. A proximal part 40 of the lever 34 is connected to the handpiece 30 and constitutes an axle about which the lever 34 is rotatable with respect to the handpiece 30. The lever 34 is spring-loaded with respect to the handpiece 30 by means of a spring 28 attached, at a first end, to the handpiece 30 and, at a second end, to the lever 34 so that rotating the lever 34 about the axle 40 involves a torque about the axle 40. Thereby the wheel 32 of the user guidance means 18 is elastically biased toward the skin 16, ensuring a firm but comfortable contact between the wheel 32 and the skin 16. The wheel 32 has a polygonal contour 22 with rounded corners, thereby providing a step roller. The contour 22 has four equal sides, each side measuring about 0.95 cm, whereas the projection of the treatment window 12 onto the moving direction measures about 1.00 cm. After the skin 16 has been exposed to a flash through the treatment window 12, the user moves the handpiece 30 in the moving direction from the device's stable position shown in FIG. 1 to a similar new stable position (not shown), thereby rotating the wheel 32 on the skin 16 about the axle 38 by an angle of 90°. The contour 22 of the wheel 32 being polygonal rather than circular, the user of the device 10 needs to overcome a palpable force in order to move the device 10 from one stable position to the next stable position. When the device 10 arrives at its new stable position, the palpable force vanishes. The vanishing of this force constitutes a tactile signal informing the user that he or she has moved the device by the step width needed to expose the next section of skin to light 14. Since the user will find the device 10 more comfortable to hold in the new position than in any of the instable interim positions, he or she will intuitively stop moving the device 10 for a moment and thereby allow for the emission of a flash of light 14 to the skin 16. The wheel 32 is preferably made of a skin compliant material. Advantageously it is made of molded plastic. The lever 34 can be made of, for example, metal, e.g. stainless steel.

Figure 2:
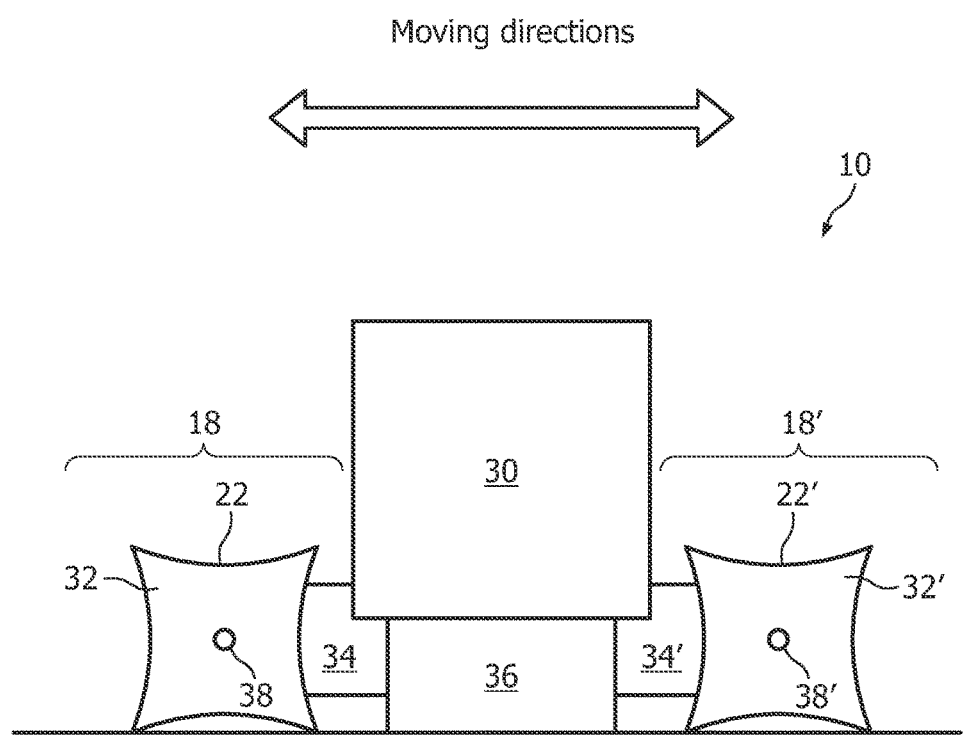
FIG. 2 is a schematic side view of another skin treatment device having a step roller comprising four square wheels having acute corners.

Referring now to FIG. 2, there is shown a side view of another embodiment of a skin treatment device according to the invention, wherein the device has two equivalent, opposite moving directions. The skin treatment device 10 includes a handpiece 30 and a hollow light guard 36 for shining light onto skin 16 via a treatment window 12, similar to the device discussed with reference to FIG. 1. Attached to the handpiece 30 via a shaft 34 is a wheel 32 rotatable about an axle 38. The shaft 34 may be designed so as to be elastic to allow for small displacements between the handpiece 30 and the axle 38. During operation of the device 10, the wheel 32 contacts the skin along its contour 22, thereby providing a step roller. The contour 22 is essentially the contour of a square having concave sides which give it a spiked appearance, each corner of the contour 22 being not rounded but acute. The four spike-like corners of the contour 22 prevent the skin treatment device 10 from sliding on the skin 16 when the device 10 is moved in one of the two moving directions, so that the wheel 32 will rotate through 90° when the device 10 is moved from one stable position on the skin 16 to a subsequent stable position. The wheel 32, the shaft 34, and the axle 38 form first guidance means 18. Second guidance means 18' comprising a second wheel 32', a second shaft 34', and a second axle 38' are arranged symmetrically with respect to the first guidance means 18 on the opposite side of the handpiece 30. The skin treatment device 10 thus has a symmetry plane orthogonal to two equivalent, opposite moving directions.

Figure 3:
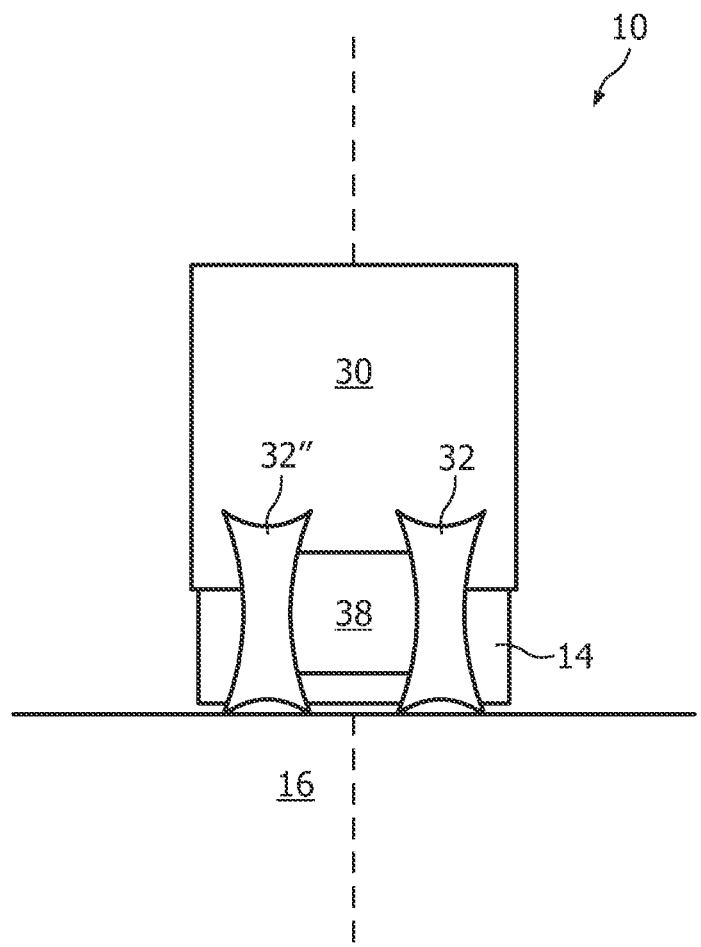
FIG. 3 is a schematic front view of the device shown in FIG. 2.

FIG. 3 provides a front view of the skin treatment device 10 discussed with reference to FIG. 2. The device has a second symmetry plane (indicated by the dashed line). Accordingly, a third wheel 32" is attached to the shaft 38. The third wheel 32" and the wheel 32 are both rotatable about the same axle 38.

Figure 4:
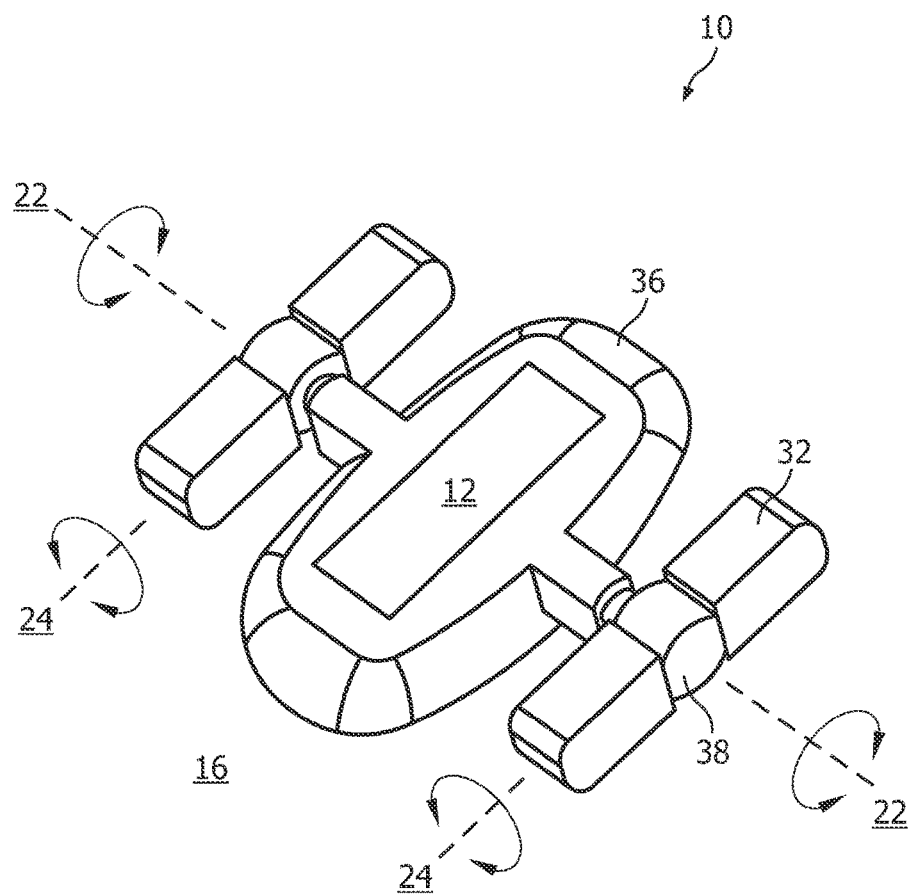
FIG. 4 is a schematic three-dimensional view of a skin treatment device incorporating two different step rollers.

FIG. 4 illustrates part of a skin treatment device 10 according to another embodiment of the invention. The skin treatment device 10 has a rectangular treatment window 12 surrounded by a hollow light guard 36. Attached to the outer shell of the light guard is first axle 38 holding a rotative cuboidal wheel 32 rotatable about the axle 38. The axle 38 is perpendicular to the longer side of the rectangular treatment window 12 and parallel to the skin 16. The cuboidal wheel's 32 contour with respect to rotation about the axle 38 defines a first step roller 22 having a step width slightly shorter than the longer side of the treatment window 12. The cuboidal wheel 32 is further rotatable about a second axle (not seen) perpendicular to the first axle 38. The second axle is perpendicular to the shorter side of the rectangular treatment window 12 and parallel to the skin 16. The cuboidal wheel's 32 contour with respect to rotation about the second axle thus defines a second step roller 24 having a step width slightly shorter than the shorter side of the treatment window 12. When the skin treatment device 10 is to be moved parallel to the longer side of the rectangular treatment window 12, the first step roller 22 provides a tactile feedback signal to the user, similar in principle to the tactile feedback signal described with reference to FIG. 1. In particular, the user feels when the device 10 has assumed a stable position on the skin 16. Analogously, when the skin treatment device 10 is to be moved parallel to the shorter side of the rectangular treatment window 12, the second step roller 24 provides tactile feedback signals to the user.

Figure 5:
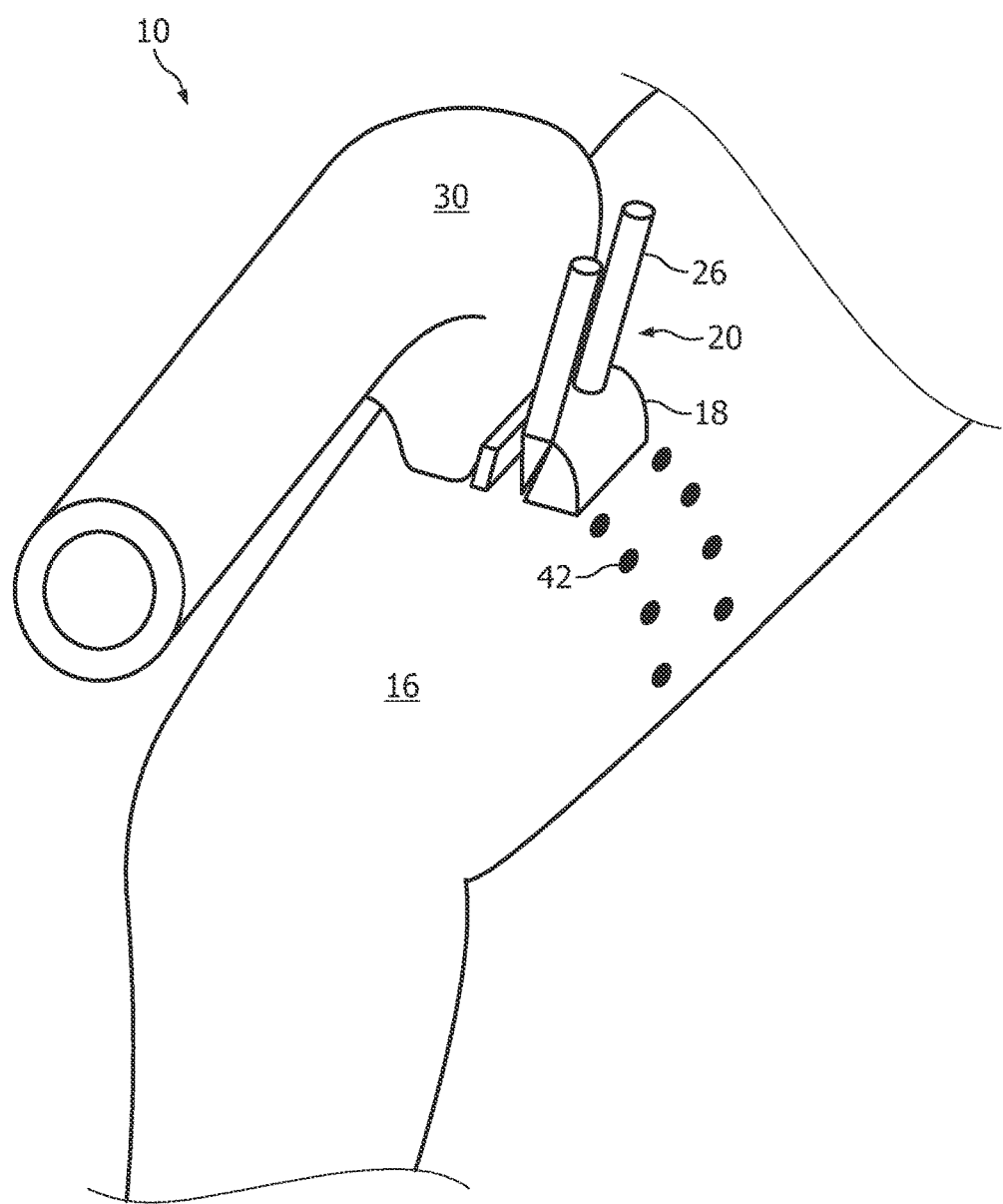
FIG. 5 is a schematic three-dimensional view of the operation of a skin treatment device having a marker.

Referring now to FIG. 5, there is schematically illustrated the operation of a skin treatment device 10 according to the invention, on a human leg, wherein the device 10 includes marking means 20 coupled to the user guidance means 18, for applying an optical mark 42 to the skin 16 during or after each moving step. The device includes an ergonomically shaped handpiece 30 and guidance means 18 to which two pencils 26 are attached, which each leave a visible dot 42 on the skin 16 each time the device is displaced over the skin from one preferred position to a subsequent preferred position as indicated by a tactile signal from the user guidance means 18. Moving the device 10 over the skin 16 thus leaves a track on the skin 16, the track consisting of two parallel lines, each line consisting of equidistant dots 42.

Figure 6:
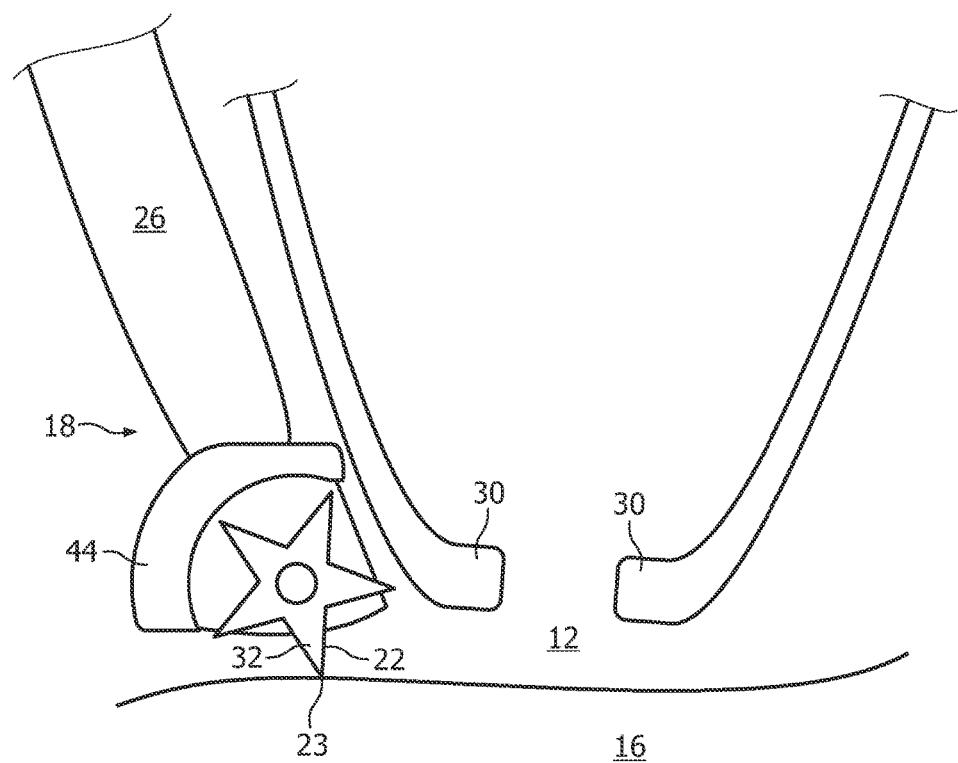
FIG. 6 is a partial schematic cut-away side view of the skin treatment device shown in FIG. 5.
Figure 7:
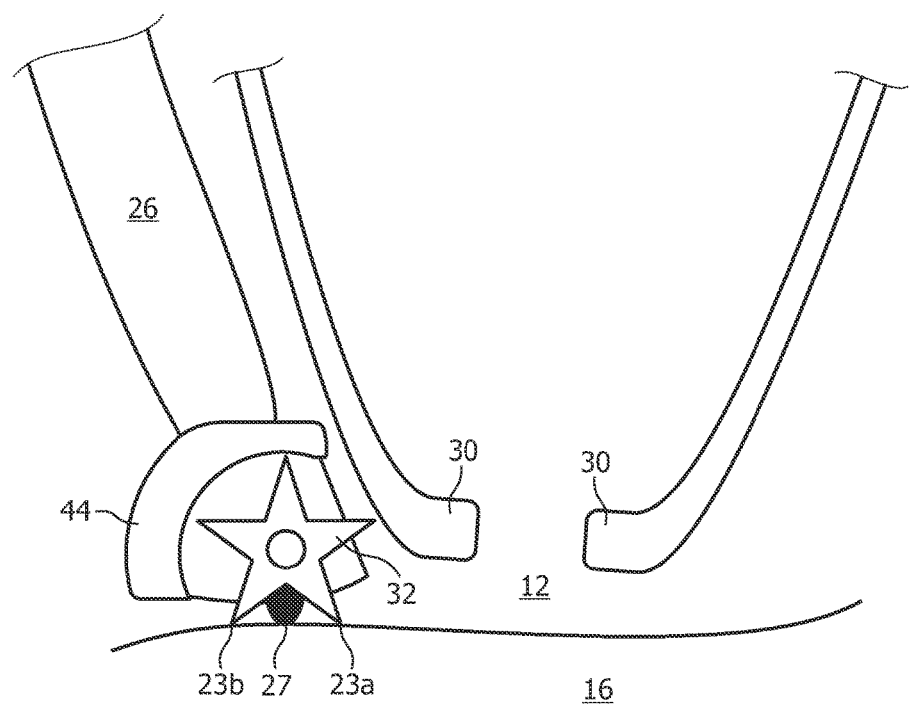
FIG. 7 is a second partial schematic cut-away side view of the skin treatment device shown in FIG. 5.

FIGS. 6 and 7 provide schematic close-up sectional views of the guidance means 18 and the pencil 26 introduced above with reference to FIG. 5. The guidance means 18 include a wheel 32 having a pentagonal contour 22 defining a step width slightly shorter than the width of the treatment window 12 of the handpiece 30. Along its upper portion, the wheel 32 is partly surrounded by a hood 44. FIG. 6 illustrates an interim position of the skin treatment device on skin, between two consecutive moving steps. In the interim situation the wheel 32 contacts the skin 16 by only one tip 23 of its pentagonal contour 22. In this situation the tip 23 protrudes beyond the pencil's 26 tip (hidden behind the wheel 32) in the direction towards the skin, thereby preventing the pencil 26 from contacting the skin. FIG. 7 shows a stable position of the skin treatment device 10, characterized in that two tips 23a and 23b of the wheel 32 contact the skin 16. In this situation, the wheel 32 no longer protrudes beyond the pencil 26, thus enabling the pencil tip 27 to contact the skin 26, so that an optical mark 42 is left on the skin 16.

Figure 8:
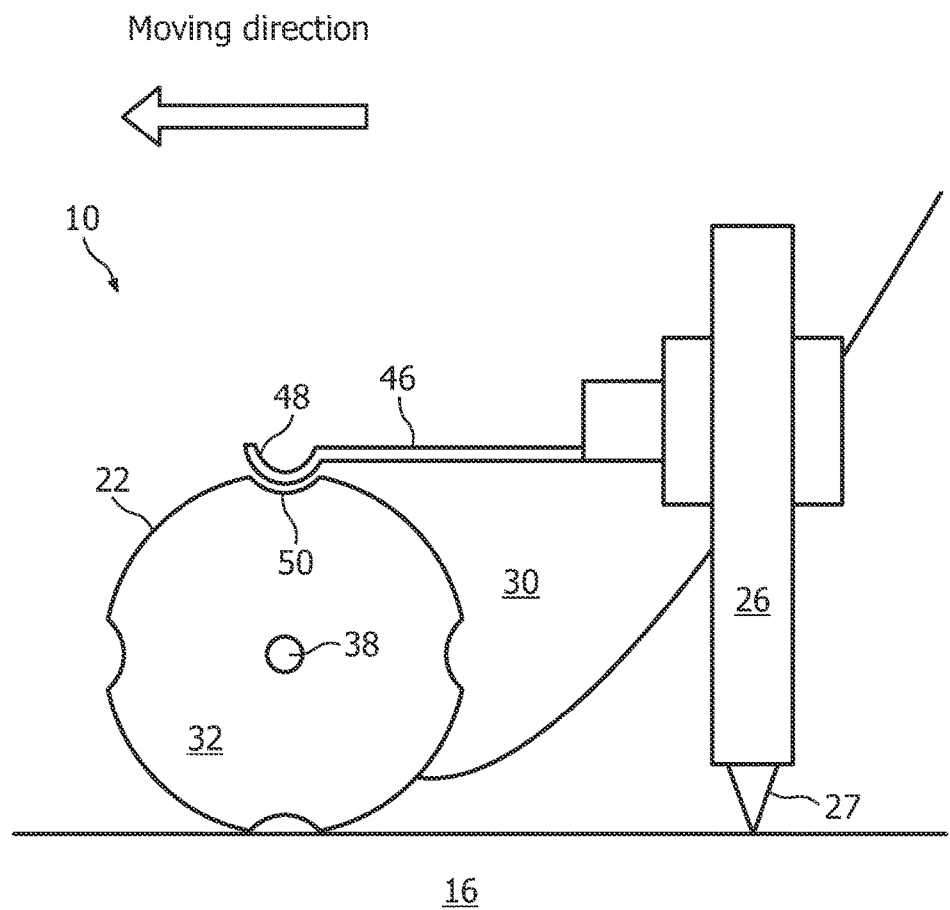
FIG. 8 is a partial schematic side view of a skin treatment device in which a marker is mechanically coupled to a step roller.

Turning now to FIG. 8, there is shown a schematic side view of a skin treatment device 10 having guidance means for delivering a tactile feedback signal, wherein the guidance means are coupled to a pencil 26 for applying a visible mark 42 on the skin 16. The guidance means include an essentially circular wheel 32 attached to a handpiece 30 by means of an axle 38. The contour 22 of the essentially circular wheel 32 has four notches spaced at angular intervals of 90°. The wheel's total circumference is slightly shorter than four times the projection of the treatment window 12 (see FIG. 9) onto the moving direction. Also attached to the handpiece 30 is a pencil 26 having a tip 27. With respect to the moving direction, the pencil 26 is situated behind the wheel 32. The pencil 26 is coupled to the wheel 32 by means of a spring leaf 46 having a distal end 48 which engages in one notch 50 of the four notches of the wheel 32 when the rotational angle of the wheel 32 with respect to the handpiece 30 comes to coincide with one of the four preferred angles defined by the notches. When the distal end 48 of the spring leaf 46 engages in one of the notches 50 of the wheel 32, the pencil tip 27 contacts the skin, thereby putting a visible mark on the skin 16. When the skin treatment device 10 is moved over the skin in the moving direction, the spring leaf 46 disengages from the notch 50. The spring leaf 46 disengaged from the notch lifts the pencil 46 from the skin 16, so that no mark is left on the skin 16 while the skin treatment device 10 is moved along the skin. The spring leaf 46 engaging with a notch 50 is felt by the user of the device as a sudden increase of the resistance of the device 10 against the user, thereby providing him or her with a tactile signal that the device 10 has reached a new position on the skin where the treatment can be continued.

Figure 9:
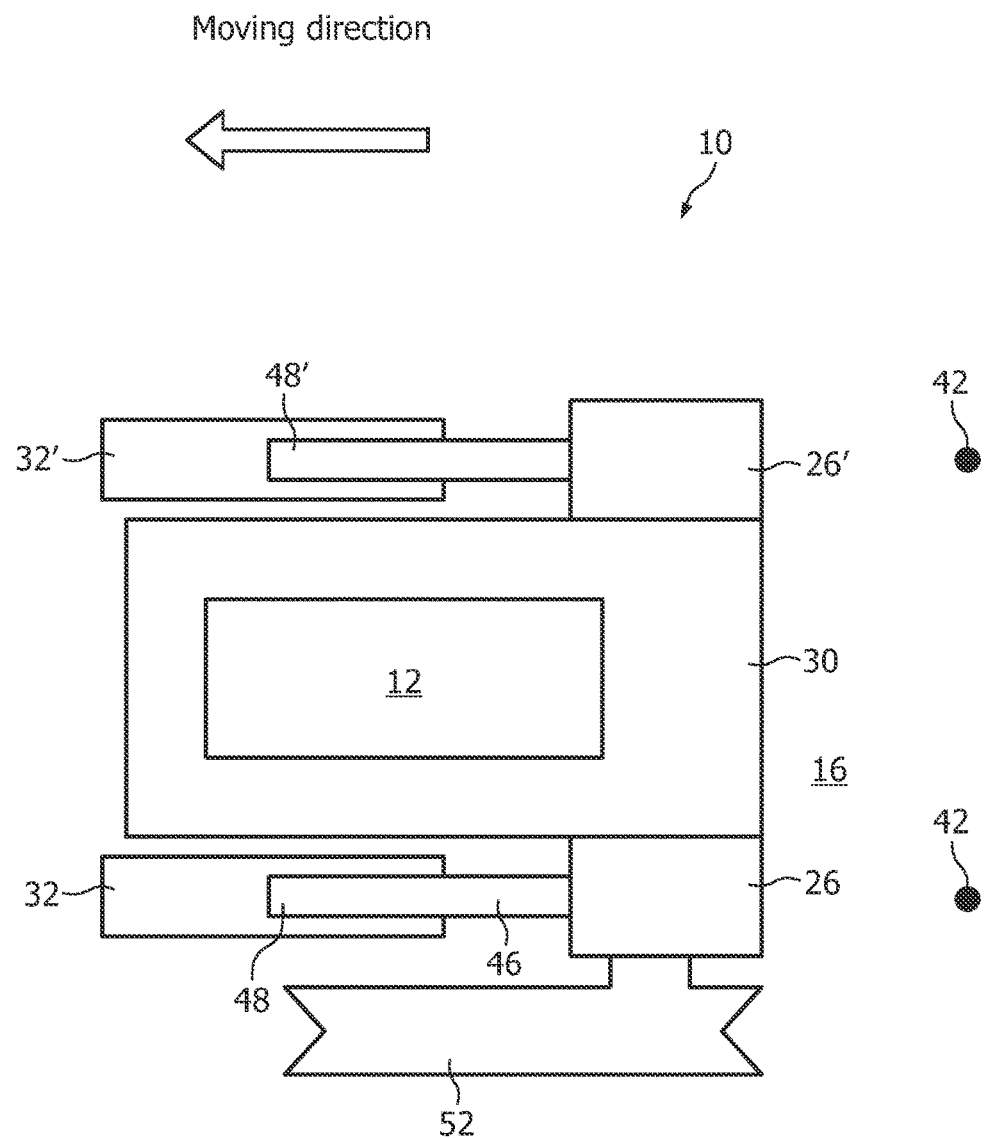
FIG. 9 is a schematic top view of the skin treatment device shown in FIG. 8.

FIG. 9 provides a schematic plan view onto the skin treatment device 10 shown in FIG. 8. For the sake of clarity, the treatment window 12 is indicated in the figure, although the window 12 is hidden under the handpiece 30. On the side opposite the side shown in FIG. 8, the device 10 has a second wheel 32' coupled to a second pencil 26' via a second leaf spring 46' in the manner described with reference to FIG. 8. The device 10 is optionally provided with a ruler 52 for repositioning the device along a mark 42 previously applied on the skin 16. A light flash through the treatment window 12 is triggered by pushing the handpiece 30 toward the skin 16 (the pushing-down mechanism for triggering the light flash is not shown).

Figure 10:
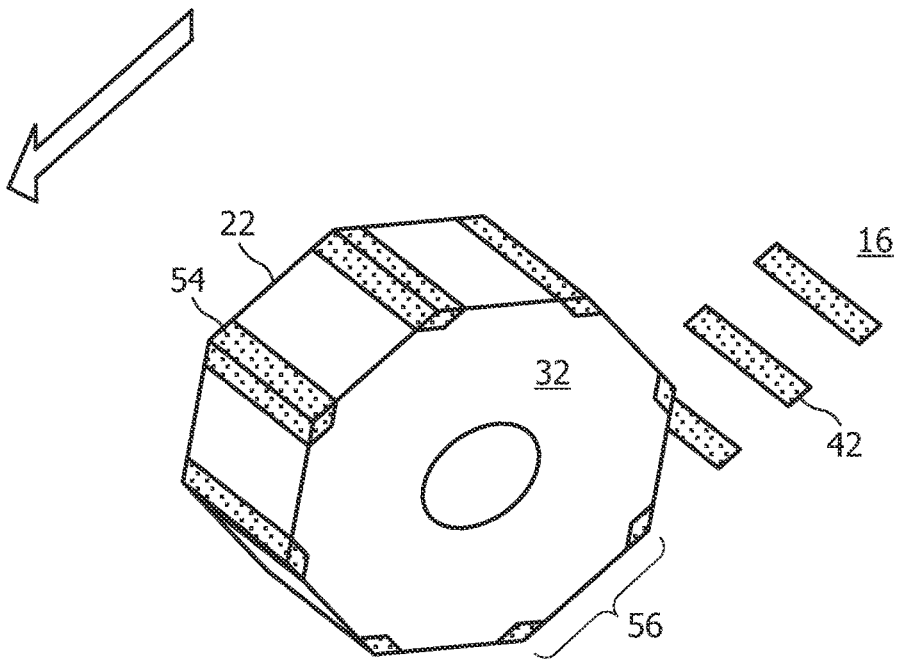
FIG. 10 is a three-dimensional view of an octagonal wheel having edges for containing a marking fluid.

Referring now to FIG. 10, there is shown a wheel 32 having an octagonal contour 22 with edges 54 designed to receive a marking fluid. According to the invention, the wheel 32 provides a step roller for a skin treatment device having a treatment window (not shown). From the preceding description of different embodiments it is clear how the wheel 32 may be arranged on the skin treatment device. Preferably, each side 56 of the wheel 32 is slightly shorter than the projection of the treatment window onto the moving direction. When the wheel 32 is rolled over the skin 16, preferably in cooperation with a handpiece 30 (not shown in this figure), visible marks 42 are left on the skin indicating the parts of the skin that have been treated. Preferably, the edges 54 contain an absorbent for containing the marking fluid. An alternative to filling the edges 54 with a marking fluid could be to integrate miniaturized pencils in the wheel 32.

Figure 11:
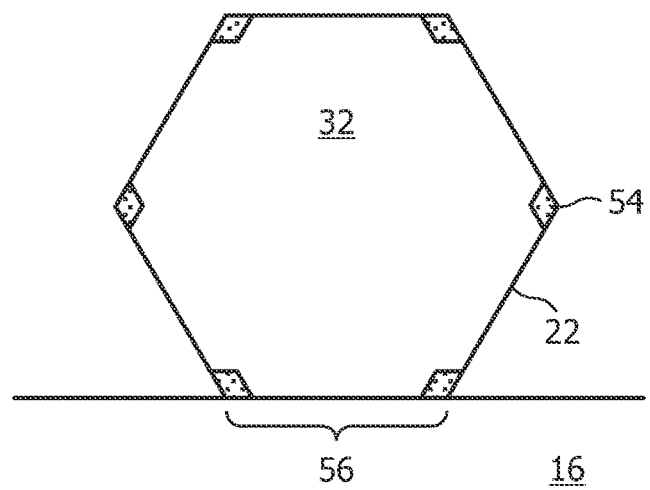
FIG. 11 is a side view of a hexagonal wheel having edges for containing a marking fluid.

FIG. 11 is a schematic side view of a wheel 32 similar to the wheel shown in FIG. 10, with a hexagonal contour 22.

Equivalents, combinations, and modifications not described above may also be realized without departing from the scope of the invention.

The invention claimed is:

1. A skin treatment device having:
 a treatment window for treating skin through the treatment window, and
 a user guide arranged separately from the treatment window, the user guide including
  an outer contour defining a step roller configured to move the treatment window along the skin in a stepwise manner, each moving step having a defined step width by which the treatment window is displaced by rolling the step roller on the skin in a stepwise manner thereby defining the step width that measures between 90% and 95%, of a projection of the treatment window onto the skin, and
  configured to deliver a tactile feedback signal in stepwise increments of the treatment window along the skin, the tactile feedback signal resulting from a physical interaction between the skin and the user guide.

2. The skin treatment device as claimed in claim 1, wherein the outer contour comprising physical surface features that require application of a palpable force to move the treatment window along the skin which force is diminished upon movement a distance of the step width from a first stable position to a second stable position.

3. The skin treatment device as claimed in claim 2, wherein the at least one step roller is replaceable by a different step roller.

4. The skin treatment device as claimed in claim 1, wherein the user guide is elastically biased to contact the skin when the skin treatment device is positioned for treating the skin.

5. The skin treatment device as claimed in claim 1, wherein the user guide is at least partly detachable from the skin treatment device.

6. The skin treatment device as claimed in claim 1, wherein the user guide is configured to trigger an emission of light via the treatment window automatically in response to moving a step.

7. The skin treatment device as claimed in claim 1, wherein the user guide is configured to trigger an optical or acoustic signal during or after each moving step.

8. The skin treatment device as claimed in claim 1, wherein the skin treatment device includes a marking device coupled to the user guide and configured to apply an optical mark to the skin as a discontinuous mark to the skin for each stepwise increment such that a plurality of stepwise increments along the skin results in a corresponding plurality of discontinuous marks.

9. The skin treatment device as claimed in claim 1, comprising a lever, wherein the user guide is coupled to the treatment window through the lever that extends the user guide away from the treatment window.

10. The skin treatment device as claimed in claim 9, comprising a handpiece, wherein the lever is coupled to the handpiece at an end proximal to the handpiece and is coupled to the user guide at an end distal to the handpiece.

11. The skin treatment device as claimed in claim 10, wherein the lever is elastically biased to press the user guide to contact the skin when the skin treatment device is positioned for treating the skin.

12. The skin treatment device as claimed in claim 1, wherein the user guide is a first user guide, the skin treatment device comprising a second user guide providing an axis of symmetry between the first and second user guides with respect to the treatment window.

13. The skin treatment device as claimed in claim 1, wherein the step roller is configured to have a step width such that the projection of the treatment window onto the skin overlaps from step to another.

* * * * *